United States Patent
Chaba et al.

(10) Patent No.: US 10,748,654 B2
(45) Date of Patent: Aug. 18, 2020

(54) NORMALIZING DATA SETS FOR PREDICTING AN ATTRIBUTE OF THE DATA SETS

(71) Applicant: PRA Health Sciences, Inc., Raleigh, NC (US)

(72) Inventors: Piotr J. Chaba, Wilmington, NC (US); Daniel J. Baker, Letchworth (GB)

(73) Assignee: PRA Health Sciences, Inc., Raleigh, NC (US)

( * ) Notice: Subject to any disclaimer, the term of this patent is extended or adjusted under 35 U.S.C. 154(b) by 0 days.

(21) Appl. No.: 15/193,676

(22) Filed: Jun. 27, 2016

(65) Prior Publication Data

US 2017/0004412 A1    Jan. 5, 2017

Related U.S. Application Data

(60) Provisional application No. 62/188,065, filed on Jul. 2, 2015.

(51) Int. Cl.
*G16H 40/20*    (2018.01)
*G16H 10/20*    (2018.01)

(52) U.S. Cl.
CPC .............. *G16H 40/20* (2018.01); *G16H 10/20* (2018.01)

(58) Field of Classification Search
CPC ................................ G16H 40/20; G16H 10/20
See application file for complete search history.

(56) References Cited

U.S. PATENT DOCUMENTS 8,626,542 B1 * 1/2014 Kapoor ............ G06Q 10/06
                                            705/7.11
2005/0055241 A1    3/2005 Horstmann
(Continued)

FOREIGN PATENT DOCUMENTS

EP     2600293 A1     6/2013
RU   2010150811 A     6/2012
(Continued)

OTHER PUBLICATIONS

Raz, Tzvi, Robert Barnes, and Dov Dvir. "A critical look at critical chain project management." Project management journal 34.4 (2003): 24-32. (Year: 2003).*

(Continued)

*Primary Examiner* — Miranda M Huang
*Assistant Examiner* — Kevin W Figueroa
(74) *Attorney, Agent, or Firm* — Kilpatrick Townsend & Stockton LLP

(57) ABSTRACT

Systems and methods are provided for improving communication by various computing systems in a network. Each computing system can be used to receive and process data. The data can be associated with a process represented by a chain of tasks. The computing systems can determine various parameters associated with the chain of tasks for determining a risk associated with the chain of tasks. The computing system can also determine a risk associated with multiple chains of tasks and aggregate the risks associated with the multiple chains of tasks. Determining the risk associated with each chain of tasks in the multiple chains of tasks can normalize a risk represented by the chains of tasks. Determining the risk associated with each chain of tasks or normalizing the risks represented by the chains can improve communication by the various computing systems in the network.

22 Claims, 9 Drawing Sheets

(56) References Cited

U.S. PATENT DOCUMENTS

| | | |
|---|---|---|
| 2006/0218012 A1 | 9/2006 | Hernandez et al. |
| 2009/0112618 A1 | 4/2009 | Johnson et al. |
| 2011/0106713 A1 | 5/2011 | Kapoor et al. |
| 2011/0292056 A1 | 12/2011 | Haas et al. |
| 2011/0313782 A1 | 12/2011 | DeMeyer et al. |
| 2014/0222492 A1* | 8/2014 | Furbeck .......... G06Q 10/06316 705/7.26 |
| 2014/0236651 A1* | 8/2014 | Sherer ............. G06Q 10/06311 705/7.13 |
| 2014/0330572 A1* | 11/2014 | Bockelman .......... G06F 19/363 705/2 |
| 2015/0324728 A1* | 11/2015 | De ....................... G06Q 10/06 705/7.15 |
| 2016/0042317 A1* | 2/2016 | Goodman .......... G06Q 10/0838 705/333 |

FOREIGN PATENT DOCUMENTS

| | | |
|---|---|---|
| WO | 2013009890 | 1/2013 |
| WO | 2017004348 A1 | 1/2017 |

OTHER PUBLICATIONS

International Patent Application No. PCT/US2016/040336, International Search Report and Written Opinion dated Sep. 30, 2016, 10 pages.

EP16818773.0 , "Extended European Search Report", dated Jan. 11, 2019, 12 pages.

PCT/US2016/040336 , "International Preliminary Report on Patentability", dated Jan. 11, 2018, 7 pages.

RU2018102378 , "Office Action", dated Jan. 18, 2019, 18 pages.

IL256552 , "Office Action", dated Jun. 24, 2019, 5 pages.

* cited by examiner

NORMALIZING DATA SETS FOR PREDICTING AN ATTRIBUTE OF THE DATA SETS

CROSS-REFERENCE TO RELATED APPLICATIONS

This disclosure claims priority to U.S. Provisional Application No. 62/188,065, titled "Early Warning System" and filed Jul. 2, 2015, the entirety of which is hereby incorporated by reference herein.

TECHNICAL FIELD

The present disclosure relates generally to computing systems. More specifically, but not by way of limitation, this disclosure relates to improving communication through data processing in computing systems by normalizing data sets for predicting an attribute of the data sets and displaying data associated with the normalized data sets.

BACKGROUND

A network of computers can include multiple computing systems or computing devices. Each of the computing systems can be used to obtain a data set (e.g., from a database), which may be associated with a process for planning or implementing a clinical trial and the computing systems may process the data set. The computing systems can communicate the data sets as the data sets are processed (e.g., as the clinical trial is implemented). The computing systems can also communicate the data sets after the data sets are processed (e.g., after a portion of the clinical trial is implemented). The computing systems can process and communicate the data set as part of the process of planning or implementing the clinical trial.

SUMMARY

In one example, a method of the present disclosure includes receiving a data set associated with a clinical trial. The data set can include data about various tasks to be completed for planning or implementing the clinical trial and a predetermined date for completing the various tasks. The method can further include storing the data set and generating a chain of tasks based on the stored data by determining a relationship between tasks within the multiple tasks and electronically converting the stored data into the chain of tasks based on the relationship. The method can further include receiving a first subset of data associated with the chain of tasks, which can include data for determining a progress of completing the chain of tasks. The method also includes determining a buffer index associated with the chain of tasks based on the first subset of data. The buffer index can correspond to a likelihood of completing the chain of tasks by the predetermined date and the buffer index can be used to determine when a processing device receives or processes an additional data set. The method further includes generating an interface for display that includes data associated with the chain of tasks, the first subset of data, or the buffer index.

In another example, a system of the present disclosure includes a processing device and non-transitory computer-readable medium that is communicatively coupled to the processing device. The processing device is configured to perform operations including receiving a data set associated with a clinical trial. The data set can include data about various tasks to be completed for planning or implementing the clinical trial and a predetermined date for completing the various tasks. The processing device is also configured to perform operations including storing the data set and generating a chain of tasks based on the stored data by determining a relationship between tasks within the multiple tasks and electronically converting the stored data into the chain of tasks based on the relationship. The processing device is also configured to perform operations including receiving a first subset of data associated with the chain of tasks, which can include data for determining a progress of completing the chain of tasks and determining a buffer index associated with the chain of tasks based on the first subset of data. The buffer index can correspond to a likelihood of completing the chain of tasks by the predetermined date and the buffer index can be used to determine when the processing device receives or processes an additional data set. The processing device is also configured to generate an interface for display that includes data associated with the chain of tasks, the first subset of data, or the buffer index.

In another example of the present disclosure, a non-transitory computer-readable medium stores program code executable by a processor device to cause a computing device to perform operations, the operations include receiving a data set associated with a clinical trial. The data set can include data about multiple tasks to be completed for planning or implementing the clinical trial and a predetermined date for completing the various tasks. The operations can further include storing the data set and generating a chain of tasks based on the stored data by determining a relationship between tasks within the multiple tasks and electronically converting the stored data into the chain of tasks based on the relationship. The operations can also include receiving a first subset of data associated with the chain of tasks, which can include data for determining a progress of completing the chain of tasks. The operations can further include determining a buffer index associated with the chain of tasks based on the first subset of data. The buffer index can correspond to a likelihood of completing the chain of tasks by the predetermined date and the buffer index can be used to determine when the computing device receives or processes an additional data set. The operations can further include generating an interface for display that includes data associated with the chain of tasks, the first subset of data, or the buffer index.

As described above, in some examples, the buffer index can be used to determine when a processing device receives or processes additional data, which can be used to manage the processing device or a network of processing devices. For example, the buffer index can be used to determine if the processing device may receive or process an additional data set sooner or later, depending on the buffer index. In some examples, using the buffer index to determine when the processing device receives or processes additional data can improve communication within a single processing device (e.g., improve intra-computing system communication within a single computing system) or improve processing operations within the single processing device (e.g., improve processor efficiency). In still another example, managing the processing device or a network of processing devices using a buffer index can include determining one or more resources that, if made available to the processing device or the network, may improve a performance of the processing device.

Managing the processing device or the network based on the buffer index can improve a performance of one or more processing devices in the network. For example, using the buffer index to determine when the processing device receives or processes additional data may allow resources of the processing device or the network to be preserved (e.g., may allow the processing device to reserve resources when the likelihood of not completing a chain of tasks by the predetermined date is low). As another example, buffer indices associated with various processing devices in the network can be used to determine an amount of data to be processed by each processing device, a time that each processing device can process an additional data set, or a duration of time that each processing device can process the additional data set. In this manner, network resources and resources of each processing device can be managed and preserved using buffer indices associated with each processing device, which may improve performance of the each processing device or the network (e.g., by reserving resources until a later time or by preserving a power of each processing device).

DETAILED DESCRIPTION

Figure 1:
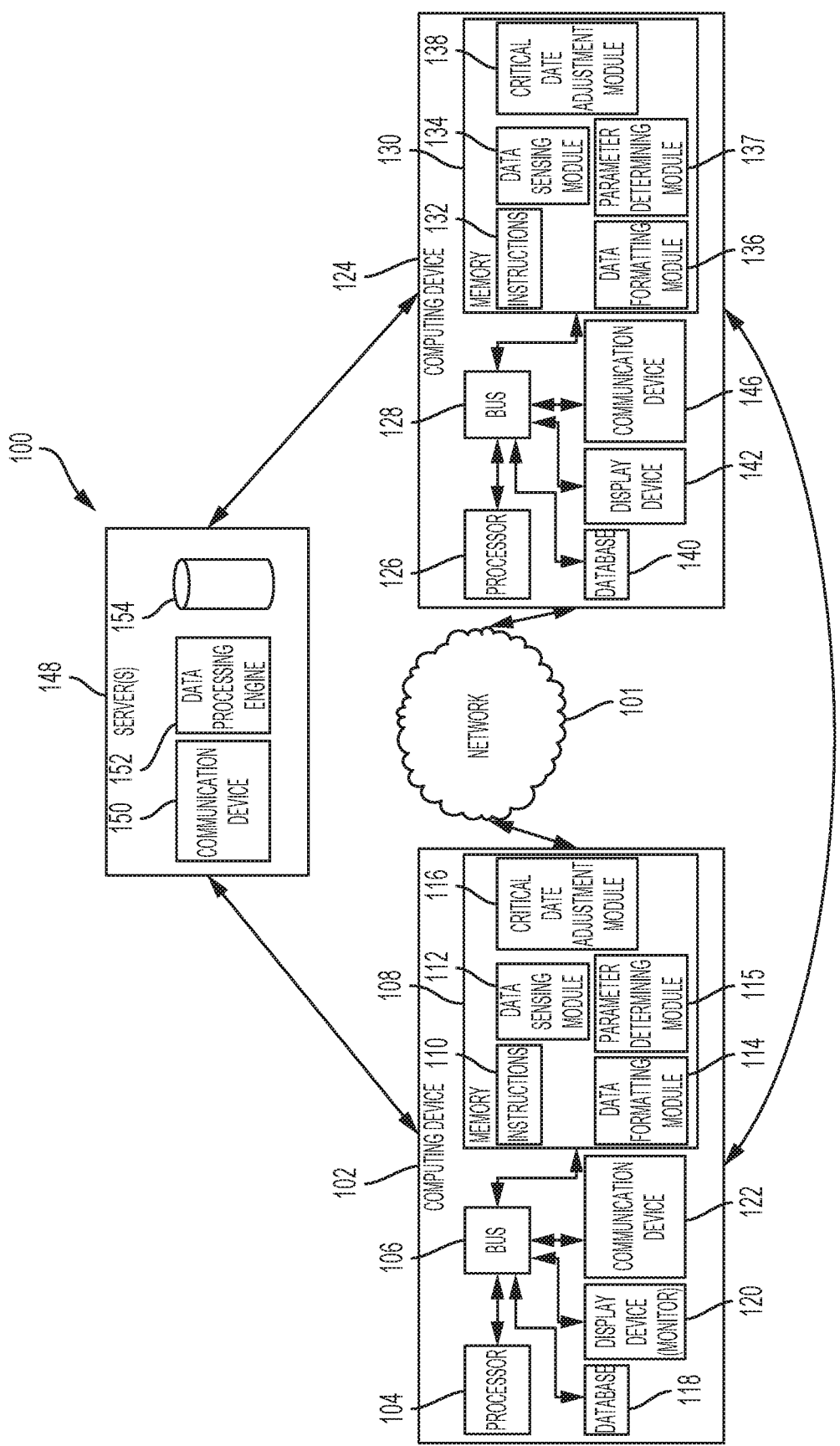
FIG. 1 is a block diagram of an example of an environment in which a network of computing devices for normalizing data sets to predict an attribute associated with the data sets operate according to some aspects.

Certain aspects and features of the present disclosure relate to normalizing data sets associated with various computing systems to predict an attribute associated with the data sets. Normalizing the data sets includes determining a risk common to the various data sets, which can be used to improve communication between the various computing systems. For example, the common risk can be used to determine when each computing system performs one or more operations on the data set associated with the computing system or on an additional data set.

In some examples, an early warning system can include the various computing systems. Each computing system can receive a data set, detect data in the data set, and process data in the data set. Each computing system can execute operations for normalizing the data sets associated with the computing system to predict an attribute associated with the data set. In some examples, normalizing the data set includes determining a risk represented by the data set and outputting a warning that can indicate the risk. The computing systems can output the warning early (e.g., prior to a condition related to the risk) to facilitate management of network resources. For example, the warning indicating the risk can be used to determine how or when each computing system electronically receives, detects, stores, or process the data set associated with the computing system or any additional data set.

In some examples, an early warning system can include a single computing system. The computing system can include multiple elements that can be used to: 1) transfer risk information between the multiple elements of the computing system and 2) standardize and make risk information comparable between multiple projects managed within the single computing system. For example, there may be two different projects and different dates, or milestones, of interest associated with each project. In certain examples, the computing system can be used to determine and assess a risk associated with each project. The computing system can also be used to determine completion dates for chains of tasks associated with each project based on a pre-set level of risk.

For example, a data set can be associated with one or more chains of tasks. Each chain of tasks can correspond to a process and include at least one task for completing the process. The data set can also include a predetermined date for completing the chains of tasks. A computing system can receive the data set and detect or store at least some data in the data set and process the detected or stored data. For example, the computing system can receive the data set and detect a subset of the data set to be stored by the computing system in a database associated with the computing system. The computing system may then process the detected or stored data by electronically converting the data into the chains of tasks based on a relationship between tasks in each chain of tasks or an order of the tasks. The computing system can also process the data by converting data about the chains or a task in each chain into an electronically readable form. The computing system can receive other data associated with a progress of completing the chains of tasks (e.g., a status of a task in a chain of tasks, an amount of time for completing the chain of tasks, etc.) and use the other data to normalize the data set by determining a risk represented by the chains of tasks (e.g., a risk of not completing the chain of tasks by the predetermined date). The computing system may communicate with other computing systems in a network while, or after processing data corresponding to the chain of tasks and normalizing the data set can improve communication by the computing systems in the network (e.g., by improving when or how the computing system receives, transmits, or processes data associated with one or more chains of tasks or additional data).

As an illustrative example, a network of various computing systems can be used to process data sets when planning or implementing a clinical trial. The data sets can correspond to a process for planning or implementing the clinical trial (e.g., a process for activating of an investigative site for the clinical trial). A data set can include multiple chains of tasks corresponding to the process and each chain of tasks can include a task for completing the process (e.g., completing site contracts, securing the required site approvals, etc.). The data set can also include a predetermine date for completing the chains of tasks. A computing system can receive the data set and other data associated with each chain of tasks. The other data can correspond to at least one of: (i) a relationship between tasks in each chain of tasks; (ii) a challenging time of a task in the chain (e.g., an amount of time for completing the task); (iii) an original buffer period of the chain (e.g., a duration of time after the challenging time of the last task in the chain); (iv) an implementation indicator of a task in the chain (e.g., a real-time status of the task or an amount of time remaining before completing the task); or (v) a critical sequence of tasks within the multiple chains of tasks (e.g., a chain of tasks among multiple chains of tasks that has the longest time or path from beginning to end). In the illustrative example, the computing system can determine a progress of each chain of tasks and various parameters associated with each chain of tasks based on the data received to determine a risk associated with the multiple chains of tasks (e.g., a risk of not completing one or more of the chains of tasks by the predetermined date). In some examples, the computing system can continuously or periodically receive other data that can be used to determine the progress of each chain of tasks and various parameters associated with each chain of tasks to determine the risk associated with the multiple chains of tasks. As an example, the computing system can periodically receive additional data that includes at least one of: (i) a relationship between tasks in each chain of tasks; (ii) the challenging time of a task in the chain; (iii) an original buffer period of the chain; (iv) an implementation indicator of a task in the chain; or (v) a critical sequence of tasks within the multiple chains of tasks as tasks in the chain of tasks are implemented or performed. The computing system may determine an updated progress of each chain of tasks or determine various updated parameters associated with each chain of tasks based on the other data received.

For example, the computing system can determine a buffer index associated with a chain of tasks, which can indicate a confidence level for completing the chain of tasks by the predetermined date. In some examples, the computing system can determine a risk level associated with the chain of tasks based on the buffer index. For example, the computing system can determine that there is a high risk of not completing the chain of tasks by the predetermined date if the buffer index is below a risk threshold. In another example, the computing system can determine that there is a low risk of not completing the chain of tasks by the predetermined date if the buffer index is above the risk threshold. The computing system can determine the corresponding buffer index for each chain of task in the multiple chains of tasks, which can be used to determine a risk of not completing each chain by the predetermined date.

Determining the buffer index for a chain of tasks within multiple chains of tasks can normalize the risk associated with the multiple chains of tasks. For example, the computing system can aggregate the buffer index for each chain of tasks within the multiple chains of tasks for normalizing the risk associated with the multiple chains of tasks. Normalizing the risk associated with the multiple chains of tasks can improve communication by computing systems in a network. For example, the aggregated buffer index can be used to determine when or how the computing system receives, transmits, or otherwise processes data associated with the multiple chains of tasks or an additional data set. Improving communication by computing systems in this manner can facilitate management of network resources for improving communications by computing systems in the network.

In some examples, the computing system can also determine a change in the predetermined date for adjusting the buffer index for a chain of tasks in the multiple chains of tasks. For example, the computing system can receive data representing a desired buffer index for the chain of tasks and determine another predetermined date that corresponds to the desired buffer index based on one or more algorithms. Changing the predetermined to adjust the buffer index can mitigate a risk associated with the chain of tasks (e.g., reduce the risk of not completing the chain of tasks).

In some examples, the computing system can generate an interface for outputting data associated with the chain of tasks, data received by the computing system, or the buffer index associated with the chain of tasks. In some examples, the computing system can output the data for selecting or implementing one or more processes for adjusting the buffer index of the chain of tasks. For example, the computing system can output data that corresponds to any data associated with the chain of tasks or a parameter of the chain of tasks for selecting a process for adjusting the buffer index.

These illustrative examples are given to introduce the reader to the general subject matter discussed here and are not intended to limit the scope of the disclosed concepts. The following sections describe various additional features and examples with reference to the drawings in which like numerals indicate like elements, and directional descriptions are used to describe the illustrative examples but, like the illustrative examples, should not be used to limit the present disclosure.

FIG. 1 is a block diagram of an example of an environment 100 in which a network of computing devices for normalizing data sets to predict an attribute associated with the data sets operate. In some embodiments, the environment 100 includes computing devices 102, 124. Each computing device 102, 124 can be positioned at a site (e.g., a site for planning or implementing a clinical trial) or offsite. Each computing device 102, 124 can receive data from another computing device (e.g., another computing device in the environment 100 or any other computing device) or an indicia of user input (e.g., if a user programs the computing device to include data). The environment also includes a network 101, which can be any network that facilitates communication of data by the computing device 102, 124 or nay other device in environment 100.

Each computing device 102, 124 can include one or more components for normalizing data sets to predict an attribute associated with the data sets. For example, the computing device 102 can include a processor 104, a bus 106, and a memory 108. The processor 104 can execute one or more operations for operating the computing device 102. The processor 104 can execute instructions 110 stored in the memory 108 to perform the operations. Non-limiting examples of the processor 104 include a Field-Programmable Gate Array ("FPGA"), an application-specific integrated circuit ("ASIC"), a microprocessor, etc.

The processor 104 can be communicatively coupled to the memory 108 via the bus 106. The memory 108 may include any time of memory device that retains stored information when powered off. Non-limiting examples of the memory 108 include electrically erasable and programmable read-only memory ("EEPROM"), flash memory, or any other type of non-volatile memory. In some examples, at least some of the memory 108 can include a computer-readable medium from which the processor 104 can read instructions 110. The computer-readable medium can include electronic, optical, magnetic, or other storage devices capable of providing the processor 104 with computer-readable instructions or other program code. Non-limiting examples of a computer readable-medium include (but are not limited to) magnetic disk(s), memory chip(s), ROM, random-access memory ("RAM"), an ASIC, a configured processor, optical storage, or any other medium from which a computer processor can read instructions. The instructions can include processor-specific instructions generated by a compiler or an interpreter from code written in any suitable computer-programming language, including, for example, C, C++, C #, etc.

In some examples, the computing device 102 can include input/output interface components (e.g., a display device 120 and a communication device 122). The computing device 102 can also include other input/output interface components such as a keyboard, a touch-sensitive surface, a mouse and additional storage.

The computing device 102 can transmit or receive data via a communication device 122. In some examples, the communication device 122 can represent one or more of any components that facilitate a network connection. In some examples, the communication device 122 may be wireless and can include wireless interfaces such as IEEE 802.11, Bluetooth, or radio interfaces for accessing cellular telephone networks (e.g., transceiver/antenna for accessing a CDMA, GSM, UMTS, or other mobile communications network). In another example, the communication device 122 can be wired and can include interfaces such as Ethernet, USB, IEEE 1394, or a fiber optic interface. The computing device 102 can transmit or receive data (e.g., transmit data to the computing device 124 or another device in the environment 100) via the communication device 122. In another example, the computing device 102 can transmit data to a remote location (e.g., an offsite location or another computing device outside the environment 100) via the communication device 122. In the example shown in FIG. 1, the computing device 102 can transmit and receive data via a wireless interface. In other examples, the computing device 102 can transmit and receive data via a wired interface.

In some examples, the memory 108 can include a data sensing module 112. The computing device 102 can use the data sensing module 112 to receive a data set. The computing device 102 can receive the data set from another computing device or system (e.g., the computing device 124, a server 148, or another computing device) or from user input (e.g., if a user programs the computing device 102 to include the data set). The data set can be associated with data for planning or implementing a clinical trial (e.g., one or more tasks associated with implementing the clinical trial). As an example, the data set can correspond to a process for: planning the clinical trial; financing the clinical trial; implementing the clinical trial; or managing the clinical trial. In some examples, the data set can include data about one or more chains of tasks that correspond to a process associated with planning or implementing the clinical trial and the chain of tasks can include at least one task for completing the process. The data set may also include a critical date for the chain of tasks (e.g., a date for completing the tasks in the chain of tasks).

In some examples, the computing device 102 can also use the data sensing module 112 to detect data in the data set. For example, the computing device 102 can use the data sensing module 112 to receive a signal (e.g., from another computing device or system) or user input that includes instructions for causing the data sensing module 112 to detect at least some data in the data set. As an example, the data set can include data associated with various processes for planning or implementing the clinical trial (e.g., a process for activating of an investigative site for the clinical trial, a process for recruiting subjects for the clinical trial, etc.) and the data sensing module 112 can detect data corresponding to the process for recruiting subjects for the clinical trial in the data set based on the signal or user input.

In some examples, the computing device 102 can use the data sensing module 112 to receive other data (e.g., from another computing device or system). The other data can be associated with one or more chains of tasks for planning or implementing the clinical trial and the other data can be used for determining a progress of completing the one or more chains of tasks. For example, the other data can correspond to at least one of: (i) a relationship between tasks in a chain of tasks, (ii) a challenging time of a task in the chain (e.g., an amount of time for completing the task), (iii) an original buffer period of the chain (e.g., a duration of time after the challenging time of the last task in the chain), (iv) an implementation indicator of a task in the chain (e.g., a real-time status of the task or an amount of time remaining before completing the task); or (v) a critical sequence of tasks within multiple chains of tasks (e.g., a chain of tasks among multiple chains of tasks that has the longest time or path from beginning to end).

In some examples, the data sensing module 112 can cause the computing device 102 to receive the data set or other data in real-time (e.g., as a task in a chain of tasks is implemented).

The data sensing module 112 can also be used to store data. For example, the data sensing module 112 can cause the computing device 102 to store at least some of the received or detected data. In some examples, the computing device 102 can store the data in a database 118.

The memory 108 can also include a data-formatting module 114, which can be used to process data. In some examples, the data-formatting module 114 can be electrically or communicatively coupled to the data sensing module 112 and can receive data detected or stored by the data sensing module 112 and process the data. In some examples, the data-formatting module 114 can be used to process the detected or stored data by electronically converting the data into a chain of tasks (e.g., the chain of tasks 301 of FIG. 3 described in detail below) that can include one or more tasks for completing a process. For example, the data-formatting module 114 can receive data about a chain of tasks and a relationship between tasks in the chain of tasks from the data sensing module 112 and the data-formatting module can electronically convert the data into a chain of tasks that corresponds to the process for planning a clinical trial and the chain of tasks can include a task for completing the process (e.g., securing required site approvals for activating a site for the clinical trial). In some examples, converting the data into the chain of tasks includes analyzing the data received to determine an order of the tasks included in the data or a relationship between the tasks and generating the chain of tasks based on the order or the relationship. For example, the data-formatting module 114 may determine that a task is a first task and another task is a second task and generate the chain of tasks based on the order of the tasks. In some examples, the data-formatting module 114 can also process data about the chain of tasks or a task in the chain and convert the data into an electronically readable form.

The memory can also include a parameter-determining module 115, which can be used to determine various parameters associated with a chain of tasks (e.g., the chain of tasks generated using the data-formatting module 114). For example, the parameter-determining module 115 can be used to determine the parameters based on data received by the computing device 102 (e.g., via the data sensing module 112). The various parameters can be used to determine a risk associated with the chain of tasks, which can be used to normalize a risk associated with multiple chains of tasks. As one example, the parameter-determining module 115 can be used to determine a buffer index associated with the chain of tasks. The buffer index can indicate a confidence level for completing the chain of tasks by the critical date of the chain of tasks. In some examples, parameter-determining module 115 can determine a risk level associated with the chain of tasks based on the buffer index. For example, the parameter-determining module 115 can determine that there is a high risk of not completing the chain of tasks by the critical date if the buffer index is below a risk threshold. In another example, the parameter-determining module 115 can determine that there is a low risk of not completing the chain of tasks by the critical date if the buffer index is above the risk threshold. In some examples, the parameter-determining module 115 can determine a buffer index associated with multiple chains of tasks and determine a rank of each chain of tasks within the multiple chains of tasks based at least in part on the buffer index associated with each chain of tasks. For example, the parameter-determining module 115 may compare a buffer index associated with a first chain of tasks with another buffer index associated with a second chain of tasks. The parameter-determining module 115 may determine a rank of the first chain of tasks and the second chain of tasks based on the comparison. The parameter-determining module 115 can determine a risk level associated with each chain of tasks within the multiple chains of tasks (e.g., a risk of not completing the chain of tasks by the critical date) based at least in part on the rank of each chain of tasks.

The memory can also include a critical date adjustment module 116. The critical date adjustment module 116 can include one or more algorithms for analyzing one or more buffer indices associated with one or more chains of tasks. The critical date adjustment module 116 can also be used to determine a change in a critical date of a chain of tasks for adjusting a buffer index of the chain of tasks. For example, the critical date adjustment module 116 can use various formulas or algorithms to determine a change in the critical date based at least in part on: (i) a desired buffer index, (ii) the critical date of the chain of tasks (iii) the original buffer period of the chain of tasks; (iv) a desired date to begin the chain of task; or (v) the amount of time remaining before completing the chain as a percentage of the chain duration. In some examples, changing the critical date to adjust a buffer index of the chain of tasks can mitigate a risk associated with the chain of tasks (e.g., reduce the risk of not completing the chain of tasks).

In some examples, the computing device 102 can generate an interface for outputting or displaying data associated with a chain of tasks, data received by the computing device, a parameter of the chain of tasks, or the buffer index associated with the chain of tasks. For example, the computing device 102 can display the data via the display device 120. In some examples, the computing device 102 can output the data for selecting or implementing one or more processes for adjusting the buffer index of the chain of tasks. For example, the computing device 102 can output data that corresponds to any data associated with the chain of tasks or a parameter of the chain of tasks for selecting a process (e.g., one or more steps) for adjusting the buffer index.

In some examples, the computing device 124 includes a processor 126, a bus 128, a memory 130, a database 140, a display device 142, and a communication device 146, each of which may be configured in substantially the same manner as the processor 104, bus 106, memory 108, database 118, display device 120, and communication device 122 of the computing device 102, although they need not be. In some embodiments, the memory 130 can include instructions 132, data sensing module 134, data-formatting module 136, parameter-determining module 137, and critical date adjustment module 138, each of which can be configured in substantially the same manner as instructions 110, data sensing module 112, data-formatting module 114, parameter-determining module 115, and critical date adjustment module 116 of computing device 102, although they need not be.

In some examples, the environment 100 can include a server 148 for storing or processing data from the computing devices 102, 124. The server 148 can be any computing system or storage device and can include a communication device 150. The communication device 150 can be configured in substantially the same manner as communication devices 122, 146. The computing devices 102, 124 can communicate with the server 148 via respective communication devices 122, 146 and the communication device 150.

In some examples, the server 148 can transmit data to each computing device 102, 124. For example, the server 148 can transmit a data set associated with data for implementing or planning a clinical trial to each computing device 102, 124. The data set can be received by the corresponding data sensing module 112, 134 of computing device 102, 124. In some examples, the computing devices 102, 124 can each transmit data to the server 148. The data can correspond to data received or detected by the data sensing modules 112, 134 of computing devices 102, 124. The data can also include data processed by the data formatting modules 114, 136 of computing devices 102, 124. For example, the computing device 102 can transmit data about the chain of tasks for the process for planning the clinical trial generated by the data-formatting module 114. The data can include various parameters of the chain of tasks determined by the computing device 102 (e.g., via parameter-determining module 115). In another example, the computing device 102 can transmit data associated with the electronically readable form of data about a task in the chain to the server 148.

The server 148 can include a data processing engine 152. The data processing engine 152 can be used to process data received by the server 148. In some examples, the data processing engine 152 can be used to process data corresponding to various parameters of a chain of tasks that can be determined by the computing devices 102, 124 (e.g., using the parameter-determining modules 115, 137). In another example, the data processing engine 152 can be used to process data corresponding to a risk level associated with the chain of tasks that can be determined by the computing devices 102, 124 (e.g., using the parameter determining-modules 115, 137). In some examples, the environment 100 may not include the server 148. In such examples, the computing devices 102, 124 may communicate (e.g., transmit and receive data), process data, or store data directly.

In some examples, each computing device 102, 124 can normalize a data set (e.g., a data set received, stored, or processed by the computing device 102, 124) to predict an attribute associated with the data set.

Figure 2:
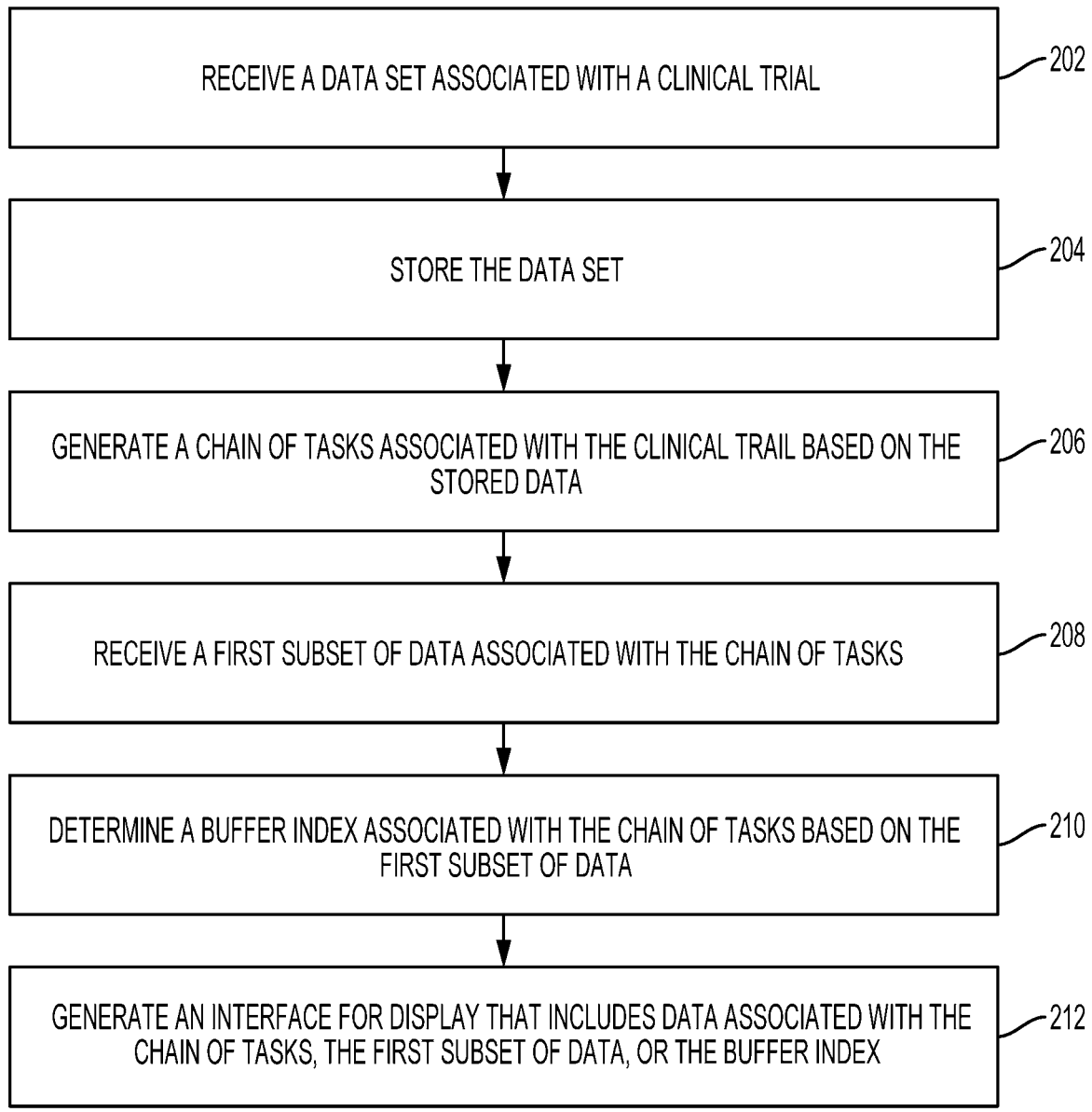
FIG. 2 is a flow chart depicting an example of a process for normalizing data sets to predict an attribute associated with the data sets according to some aspects.

FIG. 2 is a flow chart depicting an example of a process for normalizing data sets to predict an attribute associated with the data sets. The process of FIG. 2 is described with reference to the environment 100 of FIG. 1, but other implementations are possible.

In block 202, a data set associated with a clinical trial is received. In some examples, a computing device 102 receives the data set. For example, the computing device 102 can receive the data using the data sensing module 112. The computing device 102 can receive the data set from another computing device (e.g., the computing device 124 or the server 148) or from user input (e.g., if a user programs the computing device to include the data set). The data set can include data associated with one or more processes for planning or implementing the clinical trial (e.g., a process for activating of an investigative site for the clinical trial, a process for recruiting subjects for the clinical trial, etc.). In some examples, the data set includes one or more tasks to be completed for planning or implementing the clinical trial. In some examples, the data set may also include a critical date for completing the one or more tasks (e.g., a predetermined date for completing the tasks).

In block 204, the data set is stored. In some examples, the computing device 102 stores the data set. For example, the computing device 102 stores the data set using the data sensing module 112. The computing device 102 may store the detected data in a database 118 or the computing device 102 may transmit the data set to another computing device to be stored (e.g., the server 148 or the computing device 124).

In block 206, a chain of tasks associated with the clinical trial is generated based on the stored data. In some examples, the computing device 102 can generate the chain of tasks by determining a relationship between tasks in the stored data and electronically convert the stored data into the chain of tasks based on the relationship using the data-formatting module 114. For example, the computing device 102 can receive data that includes a relationship between one or more tasks in the data set (e.g., the data may indicate that a task is a first task and another task is a second task) and the computing device can generate the chain of tasks based on the relationship.

Figure 3:
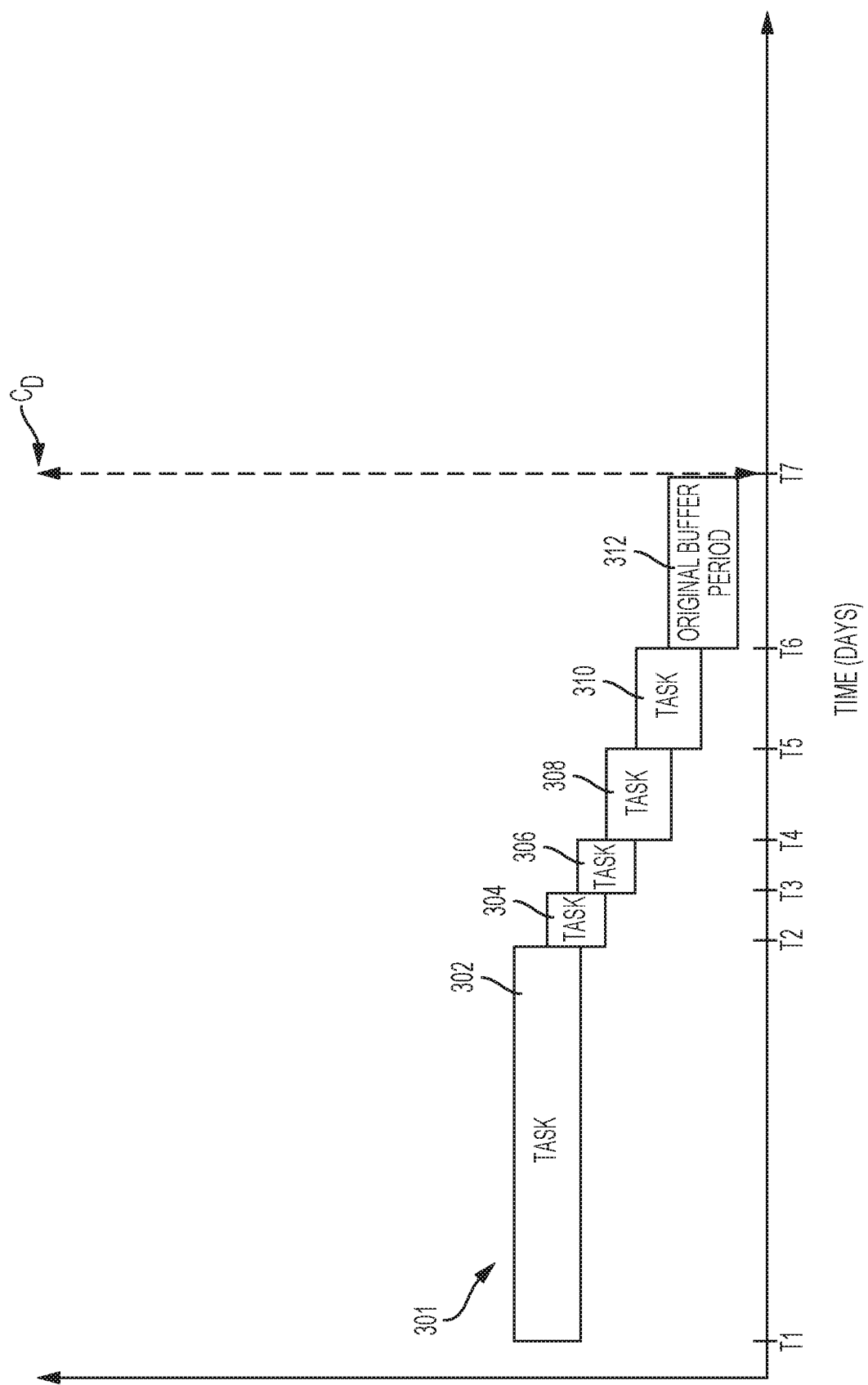
FIG. 3 is a graph depicting an example of a chain of tasks along with a critical date for the chain of tasks according to some aspects.

As an example, FIG. 3 is a graph depicting an example of a chain of tasks 301 along with a critical date for the chain of tasks. In the example depicted in FIG. 3, the computing device 102 can generate the chain of tasks 301 (e.g., in block 206 of FIG. 2). In some examples, the chain of tasks 301 corresponds to a process and includes tasks for completing the process. For example, the chain of tasks 301 can include tasks 302, 304, 306, 308, 310 each of which can represent actions or steps to be implemented for completing the process. For example, chain of tasks 301 can correspond to a process for activating an investigative site for a clinical trial. Task 302 can represent the step of completing site contracts or securing site approval. In the example depicted in FIG. 3, tasks in the chain of tasks 301 can be implemented in a sequence. For example, task 304 can be implemented after the task 302 is complete. In another example, tasks in the chain of tasks 301 can be implemented partially simultaneously. For example, task 304 and task 310 can be implemented partially simultaneously.

In some examples, each task in the chain of tasks 301 can have a challenging time. The challenging time can represent a duration of time for completing the task. For example, the task 302 can have a challenging time from $T_1$ to $T_2$. As an example, the challenging time from $T_1$ to $T_2$ can represent a duration of ten days. The task 304 can have a challenging time from $T_2$ to $T_3$, which can represent a duration of four days. The task 306 can have a challenging time from $T_3$ to $T_4$, which can represent a duration of four days. The task 308 can have a challenging time from $T_4$ to $T_5$ that represents a duration of six days. The task 310 can have a challenging time from $T_5$ to $T_6$ that represents a duration of six days.

In some examples, the chain of tasks 301 can have a chain duration. The chain duration can be a duration of time for completing the chain of tasks 301. In some examples, the chain duration can be the sum of the challenging times of tasks in the chain of tasks 301. For example, the chain duration of the chain of tasks 301 can be the sum of the challenging times of tasks 302, 304, 306, 308, 310 (e.g., 30 days).

The chain of tasks 301 can also include an original buffer period. The original buffer period can represent a duration of time after the challenging time of the last task in the chain of tasks 301. For example, the chain of tasks 301 can include an original buffer period 312. The original buffer period 312 for the chain of tasks 301 can be from $T_6$ to $T_7$, which can represent a duration of eight days. In some examples, the original buffer period 312 can provide a cushion against fluctuations or delays in completing tasks in the chain of tasks 301. Providing the cushion against fluctuations can facilitate management of the chain of tasks 301 (e.g., managing tasks in the chain of tasks 301 to assure that the chain of tasks 301 can be completed by a critical date $C_D$).

In some examples, the chains of tasks 301 can have a critical date $C_D$, which can represent a desired date for completing the chain of tasks 301 (e.g., a predetermined date for completing each task 302, 304, 306, 308, 310 in the chain of tasks 301).

Returning to FIG. 2, in some examples, in block 206, the computing device 102 can generate multiple chains of tasks associated with the clinical trial. For example, FIG. 4 is a graph depicting an example of chains of tasks 301, 303, 305 along with a critical date $C_D$ common to the chains of tasks.

Figure 4:
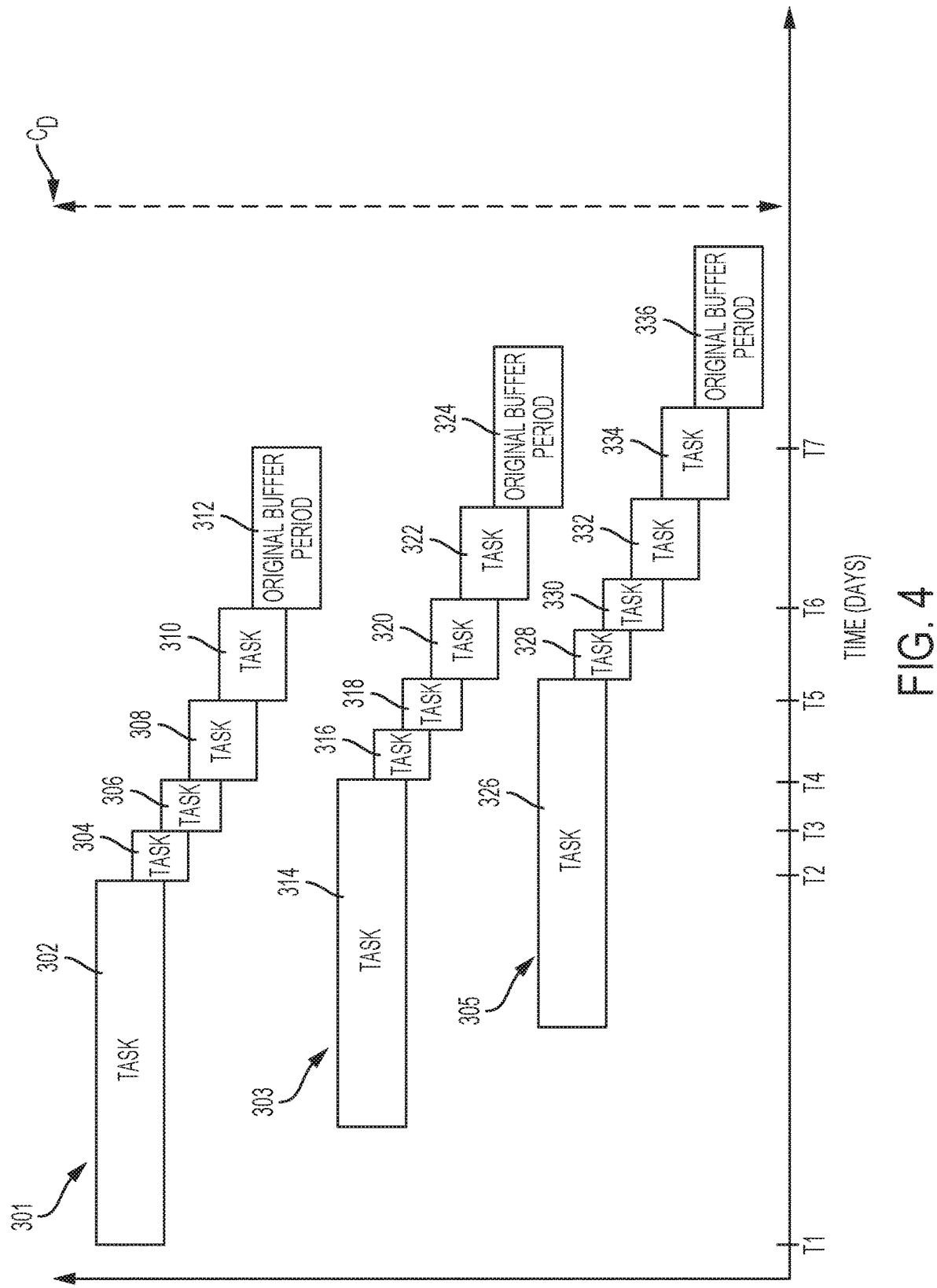
FIG. 4 is a graph depicting an example of chains of tasks along with a critical date common to the chains of tasks according to some aspects.

In the example depicted in FIG. 4, the chains of tasks 301, 303, 305 can correspond to various processes (e.g., processes for planning or implementing a clinical trial). Each chain of tasks 301, 303, 305 can include tasks for completing the various processes. For example, the chain of tasks 301 can include tasks 302, 304, 306, 308, 310. The chain of tasks 303 can include tasks 314, 316, 318, 320, 322. The chain of tasks 305 can include tasks 326, 328, 330, 332, 334. In some examples, tasks in the chains of tasks 301, 303, 305 can be implemented in a sequence. For example, task 316 in chain of tasks 303 can be implemented after task 302 in chain of tasks 301 is complete. In another example, tasks in different chains of tasks can be implemented partially simultaneously. For example, task 314 in the chain of tasks 303 and task 302 in the chain of tasks 301 can be implemented partially simultaneously. Each task in the chains of tasks 301, 303, 305 can be associated with a challenging time as described above with reference to FIG. 3. Each chain of tasks 301, 303, 305 can have a chain duration and an original buffer period 312, 324, 336 as described above with reference to FIG. 3.

In some examples, at least one of the chains of tasks 301, 303, 305 can be a critical sequence of tasks. A critical sequence of tasks can be a chain of tasks that has the longest time or longest path to complete all the tasks in the chain. For example, in FIG. 4, chain of tasks 301 can be the critical sequence of tasks in the chains of tasks. In another example, the critical sequence of tasks can be a chain of tasks involving tasks that have the greatest sum of challenging times.

In the example depicted in FIG. 4, the chains of tasks 301, 303, 305 can have a common critical date $C_D$ that represents a desired date for completing each of the chains of tasks 301, 303, 305.

Figure 5:
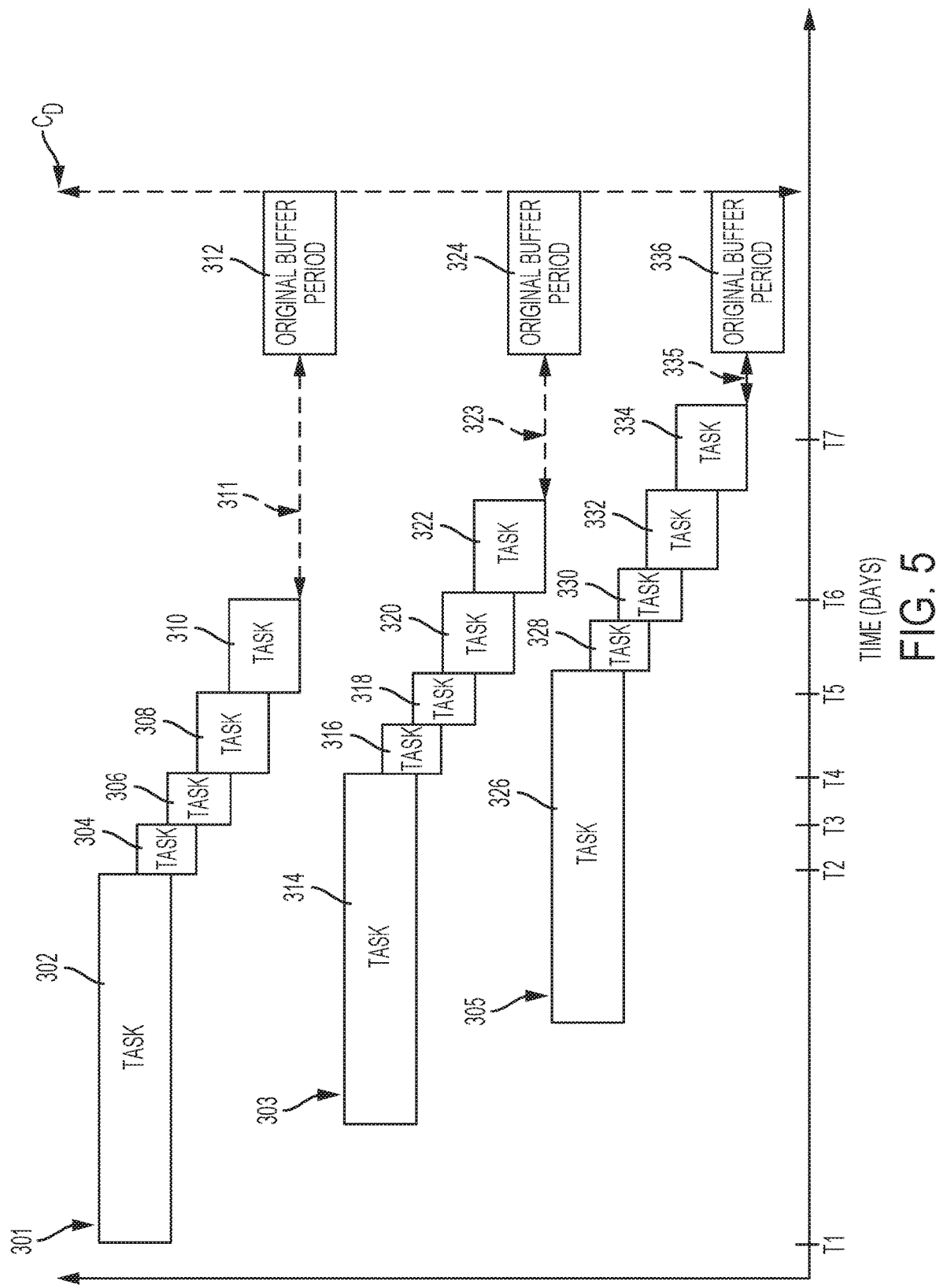
FIG. 5 is an example of a graph depicting a shift in original buffer periods of the chains of tasks of FIG. 4 according to some aspects.

With reference to FIGS. 2 and 4, in some examples, in block 208, the computing device 102 can also shift the original buffer periods 312, 324, 336 of the chains of tasks 301, 303, 305. For example, FIG. 5 is an example of a graph depicting a shift in original buffer periods 312, 324, 336 of the chains of tasks 301, 303, 305 of FIG. 4. In the example depicted in FIG. 5, the computing device 102 can shift the original buffer periods 312, 324, 336 by a corresponding duration of time 311, 323, 335. As an example, the original buffer period 312 can be shifted by the duration of time 311. The original buffer period 324 can be shifted by the duration of time 323. The original buffer period 336 can be shifted by the duration of time 335. In some examples, the computing device 102 can shift the original buffer periods 312, 324, 336 such that the end of the original buffer periods 312, 324, 336 corresponds with the critical date $C_D$ for the chains of tasks 301, 303, 305

In some examples, shifting an original buffer period of a chain of tasks can adjust a chain duration of the chain of tasks. For example, if the original buffer period is shifted, the chain duration of the chain of tasks can be the sum of the challenging times of tasks in the chain of tasks and the duration of time of the shift in the original buffer period. In the example shown in FIG. 5, a chain duration of each chain of tasks 301, 303, 305 can be adjusted by the duration of time 311, 323, 335. For example, the chain duration of chain of tasks 301 can be the sum of the challenging times of tasks 302, 304, 306, 308, 310 and the duration of time 311. The chain duration of chain of tasks 303 can be the sum of the challenging times of tasks 314, 316, 318, 320, 322 and the duration of time 323. The chain duration of chain of tasks 305 can be the sum of the challenging times of tasks 326, 328, 330, 332, 334 and the duration of time 335.

Returning to FIG. 2, in block 208, a first subset of data associated with the chain of tasks (e.g., the chain of tasks 302, 303, 305 of FIGS. 3-5) is received. In some examples, the computing device 102 receives the first subset of data from another computing device or via user input using the data sensing module 112. The first subset of data can include data about the chain of tasks or one or more tasks in the chain of tasks (e.g., task 302 of FIGS. 3-5). For example, the first subset of data can correspond to: (i) a relationship between tasks in each chain of tasks (e.g., a relationship between task 302 and task 304 of FIGS. 3-5); (ii) a challenging time of a task in the chain (e.g., a challenging time of task 302); (iii) an original buffer period of the chain of tasks (e.g., the original buffer period 312 of chain of tasks 301), (iv) an implementation indicator of a task in the chain (e.g., a real-time status of the task 302 or an amount of time remaining before completing the task 302); or (v) a critical sequence of tasks within multiple chains of tasks (e.g., a critical sequence of tasks within chains of tasks 301, 303, 305). In some examples, the first subset of data can be used to determine a progress of completing the chain of tasks (e.g., a progress of completing the chain of tasks 301).

In block 210, a buffer index associated with the chain of tasks (e.g., the chain of tasks 301, 303, 305 of FIGS. 3-5) can be determined based on the first subset of data (e.g., the first subset of data received in block 208). In some examples, the computing device 102 determines one or more parameters associated with the chain of tasks for determining the buffer index, which can be used to determine a risk associated with the chain of tasks. The risk can be a risk of not completing the chain of tasks by a specific date or a likelihood of completing the chain of tasks by the specific date (e.g., the likelihood of completing the chain of tasks 301 by the critical date $C_D$ of FIGS. 3-5).

For example, the computing device 102 can determine a chain duration of the chain of tasks based at least in part on challenging times of tasks in the chain of tasks. For example, the computing device 102 can determine the chain duration based on the sum of challenging times of the tasks in the chain (e.g., the sum of the challenging times of tasks 302, 304, 306, 308, 310 in the chain of tasks 301 of FIGS. 3-5). In some examples, the computing device 102 can determine the chain duration based at least in part on the challenging times of tasks in the chain of tasks and a shift in the buffer in the original buffer period of the chain of tasks. As an example, the computing device 102 can determine the chain duration based on the sum of: (i) a duration of time of the shift of the original buffer period (e.g., the duration of time 311 of FIG. 5); and (ii) the sum of the challenging times of tasks in the chain of tasks (e.g., the sum of the challenging times of tasks 302, 304, 306, 308, 310 in the chain of tasks 301 of FIGS. 3-5).

In some examples, the computing device 102 can determine an amount of time remaining before completing the chain of tasks (e.g., an amount of time remaining before completing the chain of tasks 301 of FIGS. 3-5). The computing device 102 can determine the amount of time remaining before completing the chain of tasks based on an implementation indicator of a task in the chain of tasks (e.g., an implementation indicator of task 302 of FIGS. 3-5), which may correspond to an amount of time remaining before completing the task. As an example, the computing device 102 can determine the amount of time remaining before completing the chain of tasks by determining a sum of: i) the amount of time remaining before completing the task; and ii) the challenging times of subsequent tasks in the chain of tasks (e.g., the challenging time of tasks 304, 306, 408, 310). For example, if there are 5 days remaining before completing the task and sum of the challenging times of subsequent tasks in the chain of tasks is 20 days, the computing device 102 can determine that the amount of time remaining before completing the chain of tasks is 30 days.

In some examples, the computing device 102 can compare the amount of time remaining before completing the chain of tasks and the chain duration. The computing device 102 can use the comparison to determine the amount of time remaining as a percentage of the chain duration. As an example, the computing device 102 can divide the amount of time remaining before completing the chain of tasks by the chain duration to determine the amount of time remaining as a percentage of the chain duration.

In some examples, the computing device 102 can determine an amount of the original buffer period remaining (e.g., an amount of the original buffer period 312 of FIGS. 3-5 remaining). In some examples, the computing device 102 can determine the amount of the original buffer period remaining in real time, as a task in the chain of tasks is implemented (e.g., as the task 302 is implemented). For example, the computing device 102 can determine the amount of the original buffer period remaining based on the implementation indicator associated with the task (e.g., the implementation indicator of task 302), which may correspond to the amount of time remaining before completing the task. The computing device 102 can subtract the amount of time remaining before the completing the task from the original buffer period to determine the amount of the original buffer period remaining. In some examples, the computing device 102 can determine a percentage of the original buffer period remaining (e.g., a percentage of the original buffer period 312 remaining). As an example, the computing device 102 can divide the amount of the original buffer period remaining by the original buffer period to determine the percentage of the original buffer period remaining.

In some examples, the computing device 102 can determine the buffer index associated with the chain of tasks (e.g., the buffer index associated with chain of tasks 301 of FIGS. 3-5) by comparing: (i) the percent of the original buffer period remaining; and (ii) the amount of time remaining before completing the chain as a percentage of the chain duration. The computing device 102 can use the comparison to determine the buffer index for the chain of tasks. As an example, the computing device 102 can divide the percent of the original buffer period remaining by the amount of time remaining before completing the chain as a percentage of the chain duration to determine the buffer index of the chain of tasks, which can indicate a confidence level for completing the chain of tasks by the critical date (e.g., a confidence of completing the chain of tasks 301 by the critical date $C_D$ of FIGS. 3-5). In some examples, the computing device 102 can determine a buffer index associated with multiple chains of tasks (e.g., a buffer index associated with each of chain of tasks 301, 303, 305). The computing device 102 may determine a rank of each chain of tasks within the multiple chains of tasks based at least in part on a buffer index of the chain of tasks. For example, the computing device 102 may determine a first buffer index associated with chain of tasks 301 and a second buffer index associated with chain of tasks 303. The computing device 102 can compare the first buffer index and the second buffer index and determine a rank of the chain of tasks 301 and a rank of the chain of tasks 303 based on the comparison. For example, the computing device 102 may rank the chain of tasks 301 first and rank the chain of tasks 303 second in response to determining that the first buffer index associated with the chain of tasks 301 is lower than the second buffer index associated with the chain of tasks 303.

In some examples, the computing device 102 can determine a risk level associated with the chain of tasks based on the buffer index. For example, the computing device 102 can determine that there is a high risk of not completing the chain of tasks by the critical date if the buffer index is below a risk threshold. In another example, the computing device 102 can determine that there is a low risk of not completing the chain of tasks by the critical date if the buffer index is above the risk threshold. In some examples, the computing device 102 can determine a risk level associated with one or more chains of task based at least in part on a rank of the one or more chains of tasks. As an example, the computing device 102 can determine the rank of the chain of tasks 301 and the rank of the chain of tasks 302 as described above and determine a risk level associated with chain of tasks 301 and chain of tasks 303. For example, the computing device 102 may rank the chain of tasks 301 higher than the chain of tasks 303 as described above, which may indicate a higher likelihood of not completing the chain of tasks 301 by the critical date as compared to the chain of tasks 303.

In some examples, the computing device 102 iteratively determines the buffer index associated with the chain of tasks. For example, the computing device 102 can receive a second subset of data that includes at least one of: (i) a relationship between tasks in each chain of tasks; (ii) the challenging time of a task in the chain; (iii) an original buffer period of the chain; (iv) an implementation indicator of a task in the chain; or (v) a critical sequence of tasks within the multiple chains of tasks as tasks in the chain of tasks are implemented or performed. The computing device 102 can determine an updated buffer index associated with the chain of tasks based on the second subset of data in substantially the same manner as described above with respect to the first subset of data. In some examples, the computing device 102 can continuously (e.g., in real-time relative to a status of a task in the chain of tasks) or periodically receive subsequent subsets of data as tasks in the chain of tasks are implemented or performed, which can allow the computing device 102 to iteratively determine or update the buffer index based on the progress of completing tasks in the chain of tasks. In this manner, the computing device 102 may provide a real-time update or status of tasks in the chain of tasks as each task in the chain of tasks is implemented, performed, or completed.

In some examples, in block 210, the computing device 102 may normalize a risk associated with multiple chains of tasks (e.g., the chains of tasks 301, 303, 305 of FIGS. 4-5). Normalizing the risk associated with the multiple chains of tasks can include aggregating a buffer index for each chain of tasks within the multiple chains of tasks. Normalizing the risk associated with the multiple chains of tasks can improve communication by computing systems in a network. For example, the aggregated buffer index can be used to determine when or how one or more computing devices (e.g., computing devices 102, 124 of FIG. 1) receives, transmits, or otherwise processes data associated with the multiple chains of tasks or an additional data set. Improving communication by computing systems in this manner may facilitate management of network resources for improving communications by the computing devices.

As described above, in some examples, a buffer index or an aggregated buffer index can be used to determine when or how one or more computing devices 102, 124 receives, transmits or otherwise processes additional data, which can be used to manage the computing devices 102, 124 or a network of one or more computing devices 102, 124. For example, the buffer index can be used to determine if the computing devices 102, 124 may process additional data sooner or later, depending on the buffer index. As an example, each computing device 102, 124 may begin processing additional data if a buffer index associated with each of the computing devices 102, 124 is above the risk threshold (e.g., there is a low risk of not completing a chain of tasks by the critical date). As another example, the computing devices 102, 124 may be delayed from processing additional data if a buffer index associate with each of the computing devices 102, 124 is below the risk threshold (e.g., there is a high risk of not completing a chain of tasks by the critical date). As another example, using the buffer index to determine when the computing devices 102, 124 receive or process additional data associated with the clinical trial can allow each of the computing devices 102, 124 to be used to process other data. In still another example, managing the computing devices 102, 124 or a network of computing devices using a buffer index can include determining one or more resource that, if made available to the computing devices 102, 124, may improve a performance of the computing devices 102, 124.

Managing the computing devices 102, 124 or a network of one or more computing devices based on a buffer index can improve a performance of each of the computing devices 102, 124. For example, using the buffer index to determine when each of the computing devices 102, 124 receives or processes additional data may allow resources of each of the computing devices 102, 124 to be preserved. As an example, using the buffer index to manage each of the computing devices 102, 124 may allow each of the computing devices 102, 124 to reserve resources (e.g., power) when the likelihood of not completing a chain of tasks by the critical date is low. As another example, buffer indices associated with each of the computing devices 102, 124 can be used to determine an amount of data to be processed by each of the computing devices 102, 124, a time that each of the computing devices 102, 124 can process an additional data set, or a duration of time that each of the computing devices 102, 124 can process the additional data set. In this manner, network resources or resources of each of the computing devices 102, 124 can be managed and preserved using buffer indices associated with the computing devices 102, 124, which may improve performance of the computing devices 102, 124 or the network (e.g., by reserving resources until a specific time or by preserving a power of each of the computing devices 102, 124).

In some examples, in block 210, the computing device 102 can determine a change in the critical date associated with one or more chains of tasks (e.g., critical date $C_D$ of FIGS. 3-5) for adjusting one or more buffer indices associated with the one or more chains of tasks (e.g., using the critical date adjustment module 116).

For example, the computing device 102 can receive data corresponding to a desired buffer index for the chain of tasks (e.g., a desired buffer index for the chain of tasks 301 of FIGS. 3-5). The computing device 102 can compare the desired buffer index to a determined buffer index. The computing device 102 can determine a change in the critical date for achieving the desired buffer index by searching for such adjusted date by step-increasing or decreasing the critical date and calculating the buffer index for each step, until it reaches the desired value of the desired buffer index. In some examples, the computing device 102 can determine a change in the critical date for achieving the desired buffer index by applying a linear or quadratic function to data determined or received by the computing device (e.g., in blocks 202-210). The computing device 102 can apply the linear or quadratic formula using a critical date adjustment module (e.g., the critical date adjustment module 116 of FIG. 1). As an example, if the desired buffer index is less than the determined buffer index, the critical date adjustment module can apply the following function to determine a change in the critical date:

$$C_{D2} = C_D + \text{BI}_{Desired} \times \text{BP}_1 \times CP$$

In the formula above, $C_D$ is the critical date of the chain of tasks, $\text{BI}_{Desired}$ is the desired buffer index, $\text{BP}_1$ is the original buffer period of the chain (e.g., original the buffer period of the chain received in block 208 of FIG. 2), CP is the amount of time remaining before completing the chain as a percentage of the chain duration (e.g., the amount of time remaining before completing the chain divided by the chain duration) and $C_{D2}$ is a new critical date for achieving the desired buffer index. As another example, if the desired buffer index is greater than the determined buffer index, the critical date adjustment module can apply the following formula to determine a change in the critical date for achieving the desired buffer index:

$$C_{D2} = C_D + \frac{-C_D + chainStartDate_{planned} + BP_1 + \sqrt{(C_D - chainStartDate_{planned} - BP_1)^2 + 4 \times \text{Duration}_{remaining} \times BP_1 \times BI_{Desired}}}{2}$$

In the formula above, $C_D$ is the critical date of the chain of tasks, $BP_1$ is the original buffer period of the chain, $\text{BI}_{Desired}$ is the desired buffer index, $chainStartDate_{planned}$ is a desired date to begin implementing the chain, $\text{Duration}_{remaining}$ is the amount of time remaining before completing the chain of tasks and $C_{D2}$ is a new critical date for achieving the desired buffer index.

In block 212, an interface for display that includes data associated with the chain of task, the first subset of data, or the buffer index is generated. In some examples, the computing device 102 can generate the interface and output the interface via a display device 120. For example, FIG. 6 is an example of a user interface 600 that can be generated by the computing device 102 for normalizing data sets to predict an attribute associated with the data sets.

Figure 6:
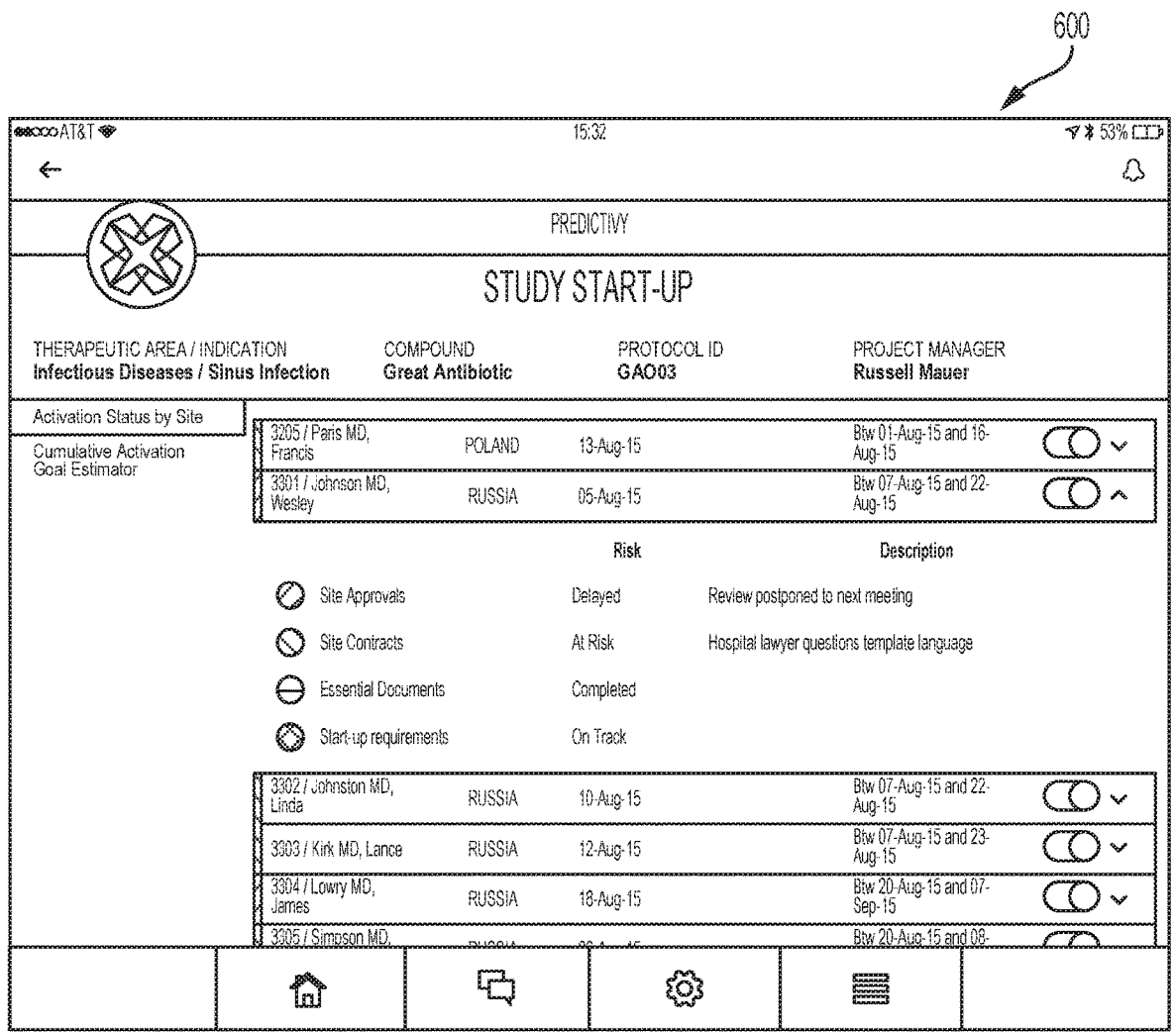
FIG. 6 is an example of a user interface that can be generated by the computing device for normalizing data sets to predict an attribute associated with the data sets according to some aspects.

In the example depicted in FIG. 6, the computing device 102 can generate the user interface 600 corresponding to data about a chain of tasks and output the user interface. The chain of tasks can correspond to a process for planning or implementing a clinical trial. For example, the user interface 600 can indicate that a chain of tasks is associated with a process for securing site approvals, securing site contracts, securing essential documents, or completing startup requirements.

In the example depicted in FIG. 6, the user interface 600 can also include a status or risk level associated with each chain of tasks. For example, the user interface 600 can indicate that a chain of tasks is at risk of not being complete by a critical date. In the example shown in FIG. 6, the user interface 600 indicates that the chain of tasks for securing site contracts is at risk of not being completed by the critical date. The user interface 600 can also indicate that the chain of tasks for securing site approvals is delayed. The user interface 600 can also indicate that the chain of tasks for securing essential documents is complete, and the chain of tasks for securing project-specific startup requirements is on track to be completed by the critical date.

In some examples, the user interface 600 generated by the computing device can also display an implementation indicator of a task in a chain of tasks. The implementation indicator can include data about the real-time status of the task. The implementation indicator may also include data that corresponds to a cause of a risk associated with the chain of tasks. In the example shown in FIG. 6, the user interface 600 can indicate that the status or cause of the risk associated with the chain of tasks for securing site approvals is that a review is postponed to a later meeting.

In the example shown in FIG. 6, the user interface can also indicate a country associated with a clinical trial and dates associated with the clinical trial.

Figure 7:
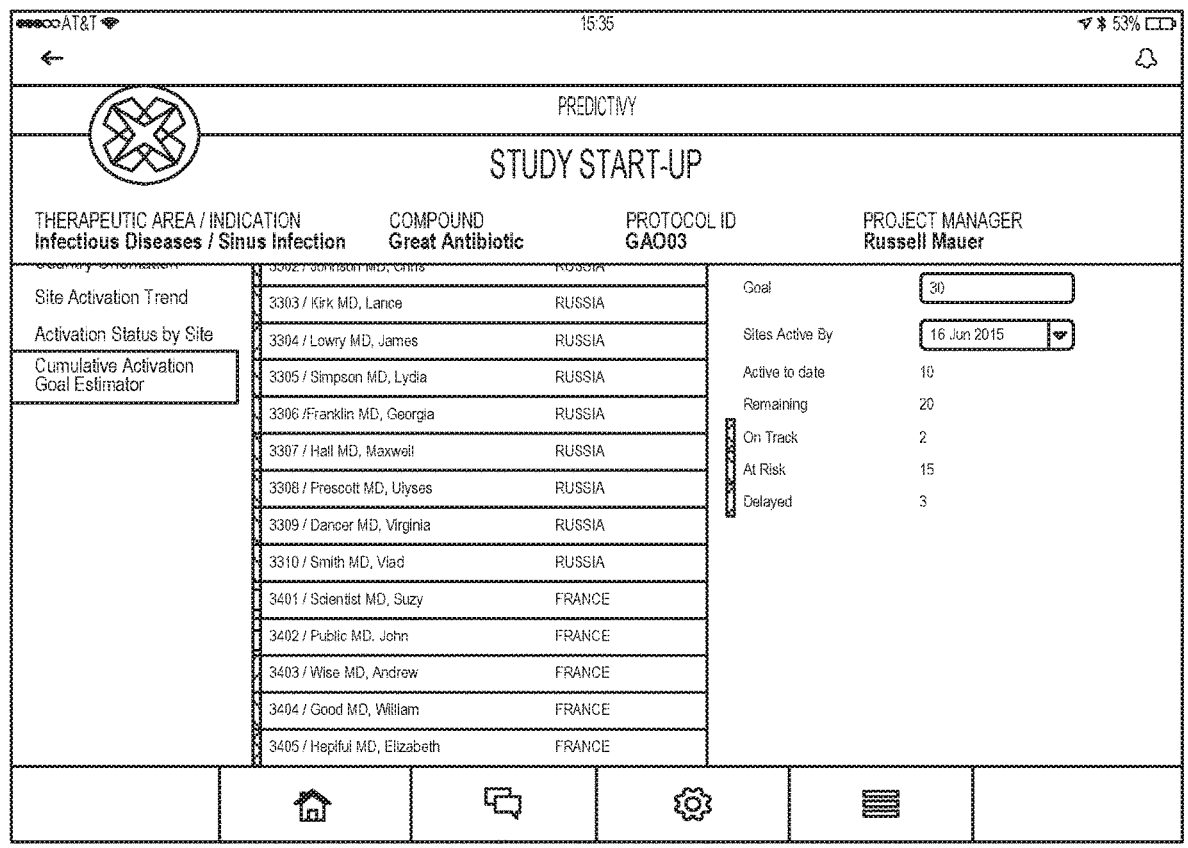
FIG. 7 is another example of a user interface that can be generated by the computing device for normalizing data sets to predict an attribute associated with the data sets according to some aspects.

FIG. 7 is another example of a user interface that can be generated by the computing device 102 for normalizing data sets to predict an attribute associated with the data sets. In the example shown in FIG. 7, the user interface can include an amount of desired sites for implementing a clinical trial, a date to have the amount of desired sites active, a name associated with each of the desired sites, a location of each of the desired sites. The user interface can also include a number of the amount of desired sites active to date, a number of the amount of desired sites remaining, a number of the amount of desired sites on track to be active by the date, a number of the amount of desired sites at risk of not being active by the date, or a number of the amount of desired sites delayed.

Figure 8:
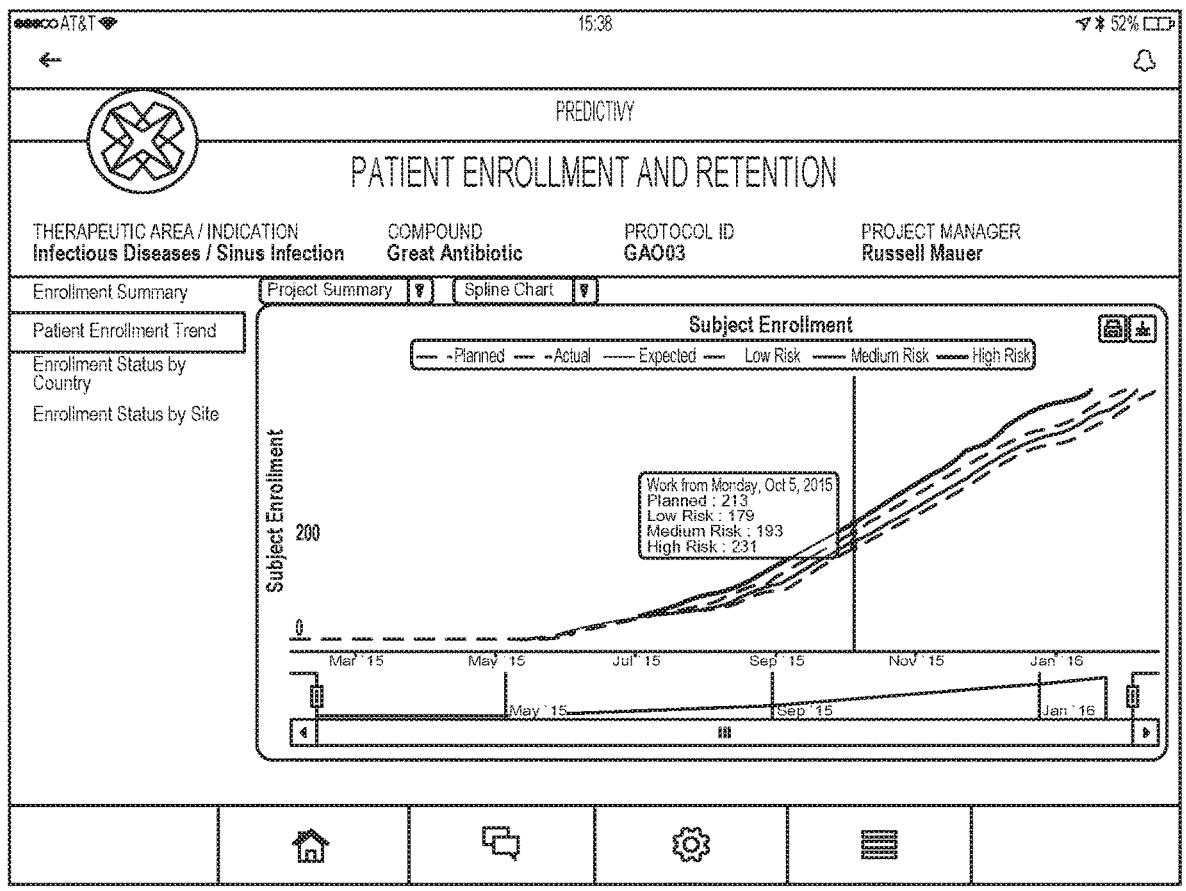
FIG. 8 is another example of a user interface that can be generated by the computing device for normalizing data sets to predict an attribute associated with the data sets according to some aspects.
Figure 9:
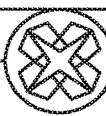
FIG. 9 is another example of a user interface that can be generated by the computing device for normalizing data sets to predict an attribute associated with the data sets according to some aspects.

FIGS. 8-9 show other examples of a user interface that can be generated by the computing device 102 for normalizing data sets to predict an attribute associated with the data sets. In the examples shown in FIGS. 8-9, the user interface can include a graph or data about subject recruitment for a clinical trial.

In some examples, the computing device 102 can generate the interface that includes data associated with the chain of task, the first subset of data, or the buffer index for determining a process or task for adjusting a parameter associated with the chain of tasks. For example, the computing device 102 can output data for determining a process or task for adjusting the buffer index of the chain of task to correspond to a desired buffer index (e.g., the desired buffer index received in block 210).

As described above, in some examples, the computing device 102 can continuously or periodically (e.g., in real-time relative to a status of a task in the chain of tasks) receive subsequent subsets of data as tasks in a chain of tasks are implemented or performed, which can allow the computing device 102 to iteratively determine or update the buffer index based on the progress of completing tasks in the chain of tasks. In this manner, the computing device 102 may provide a real-time update or status of tasks in the chain of tasks as each task in the chain of tasks is implemented, performed, or completed. In such embodiments, the computing device 102 can update a user interface generated by the computing device 102 (e.g., the user interfaces depicted in FIGS. 8-9) based on an updated status of tasks in the chain of tasks. As an example, the computing device 102 may update the user interface to indicate an updated implementation indicator of a task in a chain of tasks (e.g., a real-time status of the task or an amount of time remaining before completing the task). As another example, the computing device 102 may update the user interface to indicate an updated buffer index of the chain of tasks based on subsequent subsets of data received by the computing device 102.

The foregoing description of certain examples, including illustrated examples, has been presented only for the purpose of illustration and description and is not intended to be exhaustive or to limit the disclosure to the precise forms disclosed. Numerous modifications, adaptations, and uses thereof will be apparent to those skilled in the art without departing from the scope of the disclosure.

What is claimed is:

1. A method executed by a computing system that monitors one or more aspects of a clinical trial, the method comprising:
   receiving, by a processing device of the computing system that monitors the one or more aspects of the clinical trial, a data set associated with the clinical trial, wherein the data set specifies a plurality of tasks to be completed for planning or implementing the clinical trial and a predetermined date by which the plurality of tasks are to be completed;
   storing, by the processing device of the computing system that monitors the one or more aspects of the clinical trial, the data set in a memory device of the computing system;
   generating, by the processing device of the computing system that monitors the one or more aspects of the clinical trial, a chain of tasks based on the stored data by determining a relationship between tasks in the plurality of tasks and electronically converting the stored data into the chain of tasks based on the relationship;
   receiving, by the processing device of the computing system that monitors the one or more aspects of the clinical trial, a first subset of data associated with the chain of tasks, wherein the first subset of data indicates a progress of completing the chain of tasks;
   determining, by the processing device of the computing system that monitors the one or more aspects of the clinical trial, a buffer index associated with the chain of tasks based on the first subset of data, the buffer index being a numerical value indicating a likelihood of the chain of tasks being completed by the predetermined date;
   allocating, by the processing device of the computing system that monitors the one or more aspects of the clinical trial, computing resources for subsequent use by the processing device of the computing system based on the buffer index by adjusting an amount of the computing resources that are allocated for subsequent use by the processing device depending on the buffer index; and
   generating, by the processing device of the computing system that monitors the one or more aspects of the clinical trial, an interface for display that includes information about the chain of tasks, the first subset of data, or the buffer index.

2. The method of claim 1, further comprising:
   generating, by the processing device, a plurality of chains of tasks based at least in part on the stored data;
   determining, by the processing device, a plurality of buffer indices associated with the plurality of chains of tasks, wherein each respective buffer index among the plurality of buffer indices associated with a respective chain of tasks and is determined by:
      receiving a respective dataset corresponding to the respective chain of tasks, the respective dataset indicating a respective progress of completing the respective chain of tasks; and
      determining the respective buffer index corresponding to the respective chain of tasks based on the respective dataset, the respective buffer index indicating a respective likelihood of the respective chain of tasks being completed by the predetermined date; and
   ranking, by the processing device, the plurality of chains of tasks based on the plurality of buffer indices, each respective chain tasks being assigned a respective rank based on the respective likelihood of the respective chain of tasks being completed by the predetermined date.

3. The method of claim 1, wherein the first subset of data includes:
   a relationship indicator representing the relationship between tasks in the chain of tasks;
   a challenging time associated with a task in the chain of tasks, the challenging time corresponding to an amount of time for completing the task;
   an implementation indicator associated with the task in the chain of tasks, the implementation indicator representing an amount of time remaining before completing the task; and
   a buffer period associated with the chain of tasks, the buffer period representing an amount of time after a final task in the chain of tasks.

4. The method of claim 3, wherein determining the buffer index associated with the chain of tasks based on the first subset of data includes:
   determining, by the processing device, a chain duration based at least in part on the challenging time, the chain duration representing an amount of time for completing the chain of tasks;
   determining, by the processing device, an amount of time remaining before completing the chain of tasks based on the amount of time remaining before completing the task and a challenging time associated with another task in the chain of tasks; and determining, by the processing device, a chain percentage by comparing the chain duration and the amount of time remaining before completing the chain of tasks.

5. The method of claim 4, wherein determining the buffer index associated with the chain of tasks based on the first subset of data includes:
  determining, by the processing device, a remaining buffer period for the chain of tasks based on the implementation indicator and the buffer period by comparing the amount of time remaining before completing the task in the chain of tasks and the buffer period, wherein the remaining buffer period indicates an amount of the buffer period remaining; and
  determining, by the processing device, a buffer percentage by comparing the buffer period and the remaining buffer period.

6. The method of claim 5, wherein determining the buffer index associated with the chain of tasks based on the first subset of data further includes:
  determining, by the processing device, the buffer index by comparing the chain percentage and the buffer percentage;
  determining, by the processing device, whether the buffer index is above or below a risk threshold by comparing the buffer index to the risk threshold;
  outputting, by the processing device, data corresponding to the buffer index via the interface; and
  outputting, by the processing device, a risk level indicating the likelihood of completing the chain of tasks by the predetermined date in response to determining that the buffer index is above or below the risk threshold.

7. The method of claim 6, further comprising:
  receiving, by the processing device, a desired buffer index; and
  adjusting, by the processing device, the buffer index to a new value based on: i) the desired buffer index; ii) the predetermined date; and iii) the buffer period for the chain of tasks.

8. The method of claim 1, further comprising:
  receiving, by the processing device, a second subset of data; and
  determining, by the processing device, an updated buffer index associated with the chain of tasks based on the second subset of data, the updated buffer index corresponding to an updated likelihood of completing the chain of tasks by the predetermined date; and
  generating, by the processing device, an updated interface for display that includes data associated with the chain of tasks, the second subset of data, or the updated buffer index.

9. A system configured to monitor one or more aspects of a clinical trial, the system comprising:
  a processing device; and
  a non-transitory computer-readable medium communicatively coupled to the processing device, wherein the processing device is configured to perform operations for monitoring the one or more aspects of the clinical trial, the operations comprising:
    receiving a data set associated with the clinical trial, wherein the data set specifies a plurality of tasks to be completed for planning or implementing the clinical trial and a predetermined date by which the plurality of tasks are to be completed;
    storing the data set;
    generating a chain of tasks based on the stored data by determining a relationship between tasks in the plurality of tasks and electronically converting the stored data into the chain of tasks based on the relationship;
    receiving a first subset of data associated with the chain of tasks, wherein the first subset of data indicates a progress of completing the chain of tasks;
    determining a buffer index associated with the chain of tasks based on the first subset of data, the buffer index being a numerical value indicating a likelihood of the chain of tasks being completed by the predetermined date;
    allocating computing resources for subsequent use by the processing device of the system based on the buffer index by adjusting an amount of the computing resources that are allocated for subsequent use by the processing device depending on the buffer index; and
    generating an interface for display that includes information about the chain of tasks, the first subset of data, or the buffer index.

10. The system of claim 9, wherein the processing device is further configured to:
  generate a plurality of chains of tasks based at least in part on the stored data;
  determine a plurality of buffer indices associated with the plurality of chains of tasks, wherein each respective buffer index among the plurality of buffer indices associated with a respective chain of tasks and is determined by:
    receiving a respective dataset corresponding to the respective chain of tasks, the respective dataset indicating a respective progress of completing the respective chain of tasks; and
    determining the respective buffer index corresponding to the respective chain of tasks based on the respective dataset, the respective buffer index indicating a respective likelihood of the respective chain of tasks being completed by the predetermined date; and
  rank the plurality of chains of tasks based on the plurality of buffer indices, each respective chain tasks being assigned a respective rank based on the respective likelihood of the respective chain of tasks being completed by the predetermined date.

11. The system of claim 9, wherein the first subset of data includes:
  a relationship indicator representing the relationship between tasks in the chain of tasks;
  a challenging time associated with a task in the chain of tasks, the challenging time corresponding to an amount of time for completing the task;
  an implementation indicator associated with the task in the chain of tasks, the implementation indicator representing an amount of time remaining before completing the task; and
  a buffer period associated with the chain of tasks, the buffer period representing an amount of time after a final task in the chain of tasks.

12. The system of claim 11, wherein the processing device is further configured to determine the buffer index associated with the chain of tasks based on the first subset of data by:
  determining a chain duration based at least in part on the challenging time, the chain duration representing an amount of time for completing the chain of tasks;
  determining an amount of time remaining before completing the chain of tasks based on the amount of time remaining before completing the task and a challenging time associated with another task in the chain of tasks; and determining a chain percentage by comparing the chain duration and the amount of time remaining before completing the chain of tasks.

13. The system of claim 12, wherein the processing device is further configured to determine the buffer index associated with the chain of tasks based on the first subset of data by:
determining a remaining buffer period for the chain of tasks based on the implementation indicator and the buffer period by comparing the amount of time remaining before completing the task in the chain of tasks and the buffer period, wherein the remaining buffer period indicates an amount of the buffer period remaining; and
determining a buffer percentage by comparing the buffer period and the remaining buffer period.

14. The system of claim 13, wherein the processing device is further configured to determine the buffer index associated with the chain of tasks based on the first subset of data by:
determining the buffer index by comparing the chain percentage and the buffer percentage;
determining whether the buffer index is above or below a risk threshold by comparing the buffer index to the risk threshold;
outputting data corresponding to the buffer index via the interface; and
outputting a risk level indicating the likelihood of completing the chain of tasks by the predetermined date in response to determining that the buffer index is above or below the risk threshold.

15. The system of claim 14, wherein the processing device is further configured to:
receive a desired buffer index; and
adjust the buffer index based on i) the desired buffer index; ii) the predetermined date; and iii) the buffer period for the chain of tasks.

16. A non-transitory computer-readable medium storing program code that is executable by a processing device of a computing system configured to manage one or more aspects of a clinical trial, the program code being executable for causing the processing device to perform operations comprising:
receiving a data set associated with the clinical trial, wherein the data set specifies a plurality of tasks to be completed for planning or implementing the clinical trial and a predetermined date by which the plurality of tasks are to be completed;
storing the data set;
generating a chain of tasks based on the stored data by determining a relationship between tasks in the plurality of tasks and electronically converting the stored data into the chain of tasks based on the relationship;
receiving a first subset of data associated with the chain of tasks, wherein the first subset of data indicates a progress of completing the chain of tasks;
determining a buffer index associated with the chain of tasks based on the first subset of data, the buffer index being a numerical value indicating a likelihood of the chain of tasks being completed by the predetermined date;
allocating computing resources for subsequent use by the processing device of the computing system based on the buffer index by adjusting an amount of the computing resources that are allocated for subsequent use by the processing device depending on the buffer index; and generating an interface for display that includes information about the chain of tasks, the first subset of data, or the buffer index.

17. The non-transitory computer-readable medium of claim 16, further comprising program code to cause the computing system to perform the operations of:
generating a plurality of chains of tasks based at least in part on the stored data;
determining a plurality of buffer indices associated with the plurality of chains of tasks, wherein each respective buffer index among the plurality of buffer indices associated with a respective chain of tasks and is determined by:
receiving a respective dataset corresponding to the respective chain of tasks, the respective dataset indicating a respective progress of completing the respective chain of tasks; and
determining the respective buffer index corresponding to the respective chain of tasks based on the respective dataset, the respective buffer index indicating a respective likelihood of the respective chain of tasks being completed by the predetermined date; and
ranking the plurality of chains of tasks based on the plurality of buffer indices, each respective chain tasks being assigned a respective rank based on the respective likelihood of the respective chain of tasks being completed by the predetermined date.

18. The non-transitory computer-readable medium of claim 16, wherein the first subset of data includes:
a relationship indicator representing the relationship between tasks in the chain of tasks;
a challenging time associated with a task in the chain of tasks, the challenging time corresponding to an amount of time for completing the task;
an implementation indicator associated with the task in the chain of tasks, the implementation indicator representing an amount of time remaining before completing the task; and
a buffer period associated with the chain of tasks, the buffer period representing an amount of time after a final task in the chain of tasks.

19. The non-transitory computer-readable medium of claim 18, wherein the operation of determining the buffer index associated with the chain of tasks based on the first subset of data includes:
determining a chain duration based at least in part on the challenging time, the chain duration representing an amount of time for completing the chain of tasks;
determining an amount of time remaining before completing the chain of tasks based on the amount of time remaining before completing the task and a challenging time associated with another task in the chain of tasks; and
determining a chain percentage by comparing the chain duration and the amount of time remaining before completing the chain of tasks.

20. The non-transitory computer-readable medium of claim 19, wherein the operation of determining the buffer index associated with the chain of tasks based on the first subset of data includes:
determining a remaining buffer period for the chain of tasks based on the implementation indicator and the buffer period by comparing the amount of time remaining before completing the task in the chain of tasks and the buffer period, wherein the remaining buffer period indicates an amount of the buffer period remaining;

determining a buffer percentage by comparing the buffer period and the remaining buffer period;

determining the buffer index by comparing the chain percentage and the buffer percentage;

determining whether the buffer index is above or below a risk threshold by comparing the buffer index to the risk threshold; and determining a risk level indicating the likelihood of completing the chain of tasks by the predetermined date based on whether the buffer index is above or below the risk threshold; and outputting the risk level.

21. The method of claim 1, wherein the buffer index is determined based on (i) a buffer percentage specifying how close a buffer period is to being completed, and (ii) a chain percentage specifying how close the chain of tasks is to being completed in its entirety.

22. The method of claim 21, wherein the buffer index is determined by dividing the buffer percentage by the chain percentage.

* * * * *